United States Patent [19]

Lin et al.

[11] 4,298,592

[45] Nov. 3, 1981

[54] DOUBLE ANTIBODY SEPARATION METHOD

[75] Inventors: Wayne H. T. Lin, Chesterfield; James J. Grib; Larry D. Mosier, both of St. Louis, all of Mo.

[73] Assignee: Mallinckrodt, Inc., St. Louis, Mo.

[21] Appl. No.: 27,387

[22] Filed: Apr. 5, 1979

[51] Int. Cl.$^3$ .................. G01N 33/48; G01T 1/00; A61K 43/00; B65D 71/00

[52] U.S. Cl. .................................. 424/1; 23/230 B; 422/61; 424/12; 435/7; 435/17; 435/21

[58] Field of Search ................ 435/7, 17, 21; 23/230 B; 424/1, 1.5, 12; 422/61

[56] References Cited

U.S. PATENT DOCUMENTS

| | | | |
|---|---|---|---|
| 3,995,019 | 11/1976 | Jerome | 424/1.5 |
| 4,018,883 | 4/1977 | Parslow | 424/1 |
| 4,139,604 | 2/1979 | Gutcho et al. | 424/1 |

OTHER PUBLICATIONS

Chard, An Introduction to Radioimmuno Assay and Related Techniques, North Holland Pub. Co., Amsterdam, 1978, pp. 410–417.

Remes et al., Radio Chem. Radioanal Letters, 34(2-4),pp. 253–260 (1978).

Blank-uss et al, Clinica Chimica Acta, 86, pp. 67–72 (1978).

*Primary Examiner*—Brooks H. Hunt
*Assistant Examiner*—Christine M. Nucker
*Attorney, Agent, or Firm*—Bernard, Rothwell & Brown

[57] ABSTRACT

A double antibody radioimmunoassay method for determining antigens in a sample wherein polyethylene glycol is provided in a reaction medium to accelerate an immunoprecipitation reaction between water-soluble first antibodies bound to antigen and water-soluble second antibodies which are not specific to said antigens but which are specific to said first antibodies. A double antibody, multi-component radioimmunoassay test kit is also provided. The kit contains radiolabeled antigen reagent, first water-soluble antibody reagent and second water-soluble antibody reagent, as well as a polyethylene glycol reagent, which may optionally be combined with the second antibody reagent, in an amount sufficient to accelerate an immunoprecipitation reaction, between said first and second reagents.

9 Claims, 3 Drawing Figures

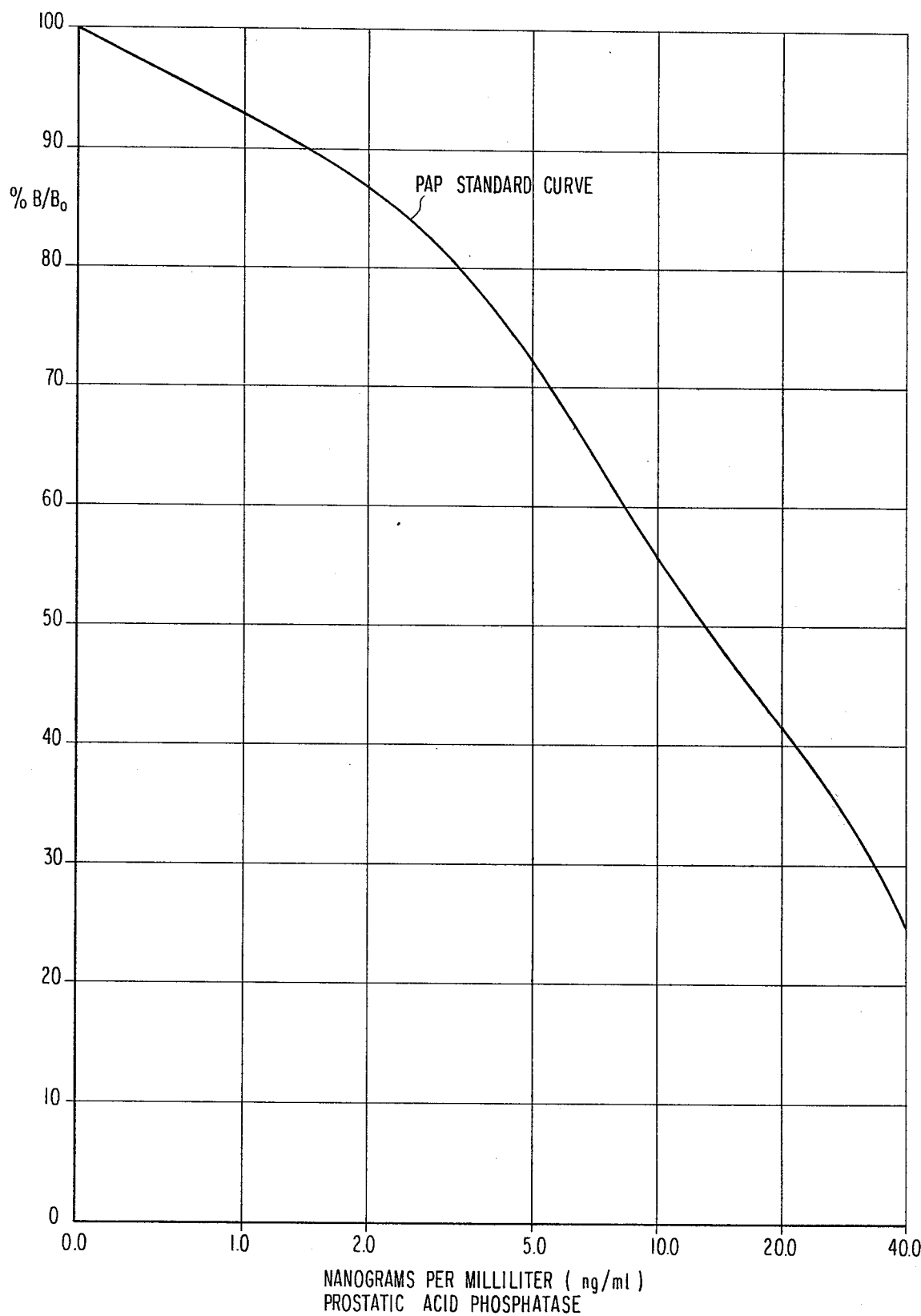

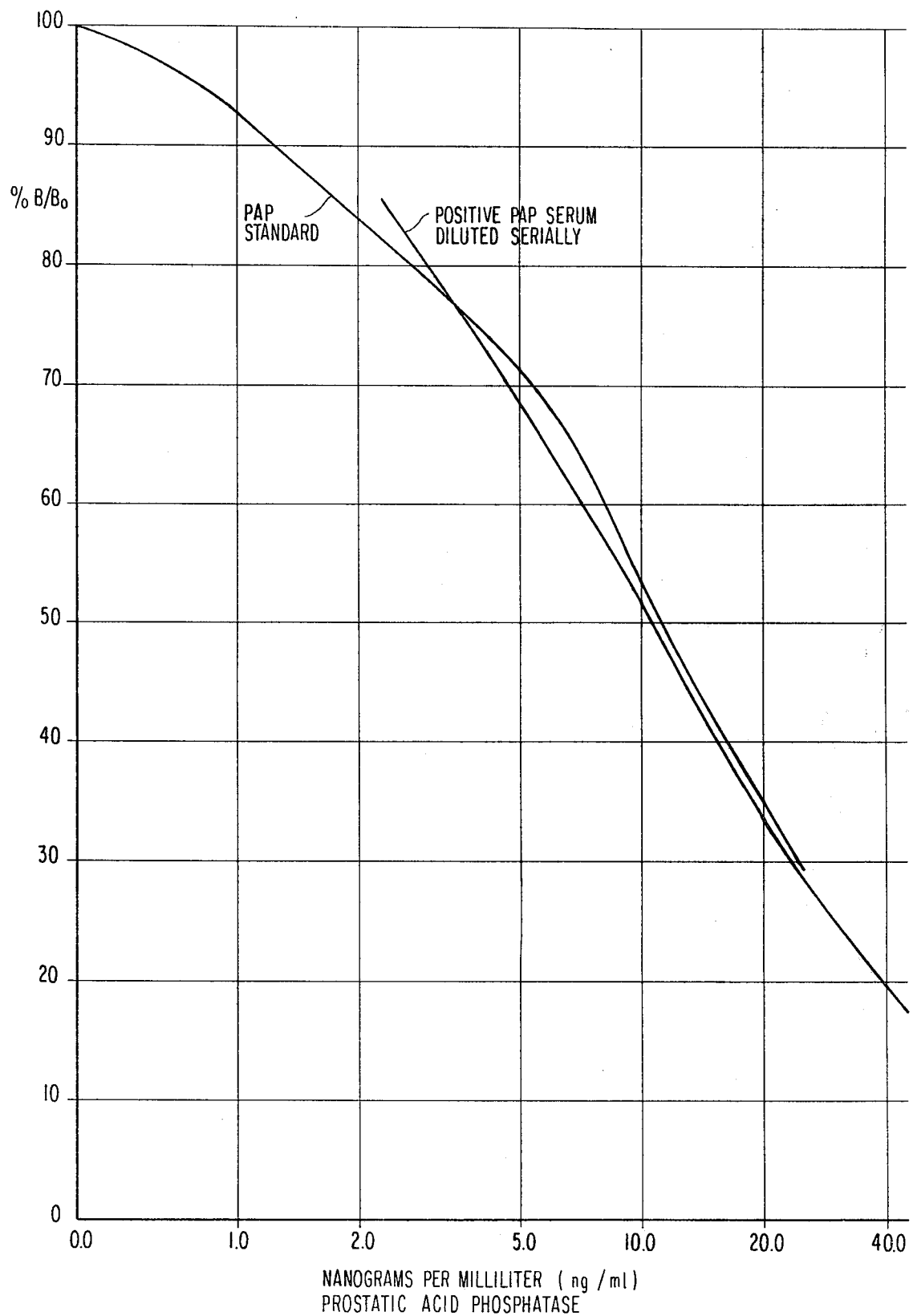
FIG. II – RELATIONSHIP BETWEEN POSITIVE PAP SERUM DILUTED SERIALLY AND PAP STANDARD CURVE

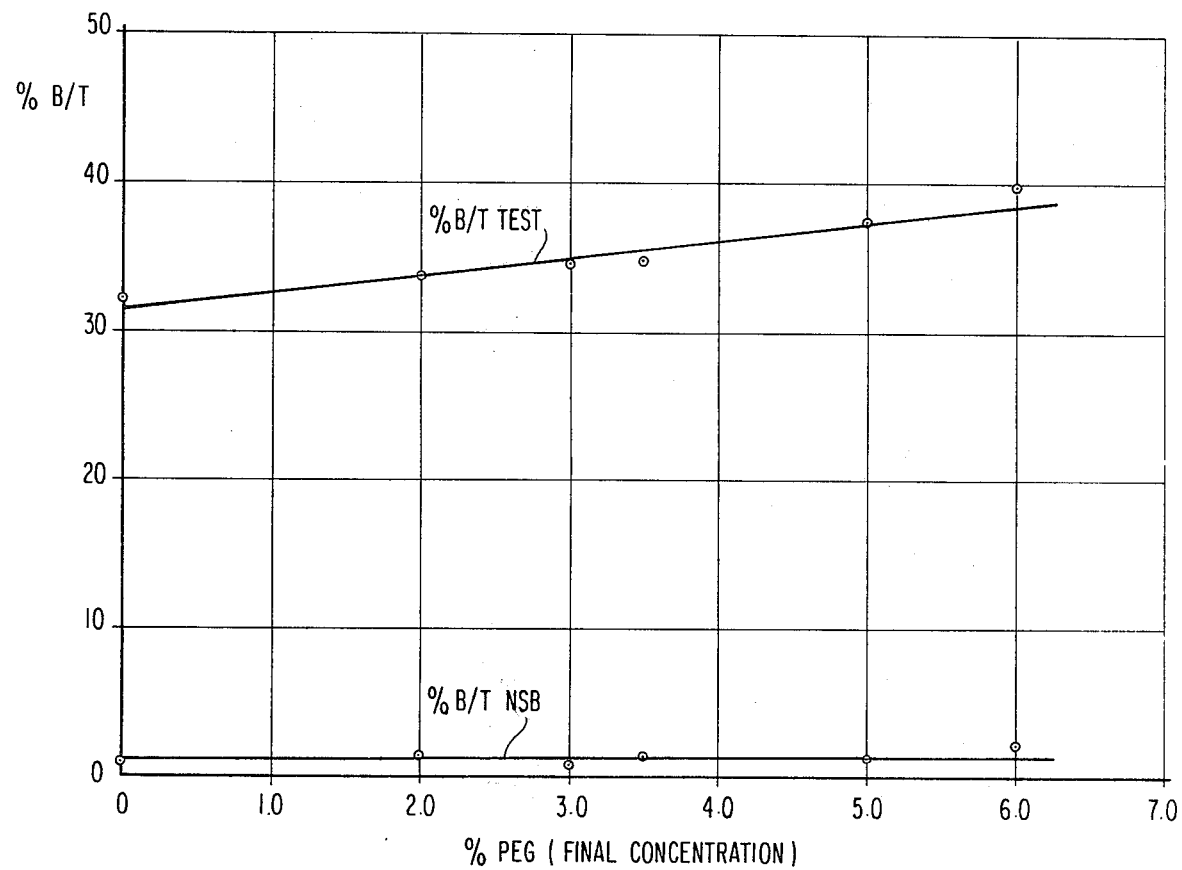
FIG. III — EFFECT OF POLYETHYLENE GLYCOL (PEG) CONCENTRATION IN SEPARATING ANTIGEN/ANTIBODY COMPLEX FROM FREE ANTIGEN IN CREATINE PHOSPHOKINASE TEST

DOUBLE ANTIBODY SEPARATION METHOD

This invention relates to a reagent and method for use in the assay of antigens and similar substances having antigenic activity.

In recent years a number of clinical diagnostic tests have been developed which employ radioisotope-labeled materials. These tests have been adapted to the determination of small concentrations of various components of blood serum and other biological fluids. In the diagnostic technique known as radioimmunoassay (RIA), anitigen is measured by its effect on the binding of a small quantity of radioactive tracer antigen to a predetermined amount of specific antibody. This RIA technique must include some procedure for separating antibody-bound antigen from the unbound antigen after completion of the immune reaction, whereby the radioactivity of the separated components can be determined by scintillation counting.

Various procedures have been developed for separating the bound and unbound antigen components in RIA techniques. Selective adsorption of the free antigen component may be achieved by the use of a particulate adsorbent such as charcoal, or by the use of inorganic crystalline adsorbents in colloidal form such as magnesium carbonate or silica. Other known procedures employ ion exchange resins having strongly basic amino or quaternary ammonium groups or a resin in a polyurethane sponge. Still other methods employ covalent bonding of the antibody to water-insoluble polymers such as dextran and Sephadex (a trademark of Pharmacia AB, Uppsala, Sweden) as set forth in U.S. Pat. No. 3,555,143; or a nonspecific physical bonding to various polymers as disclosed in U.S. Pat. No. 3,790,663; or entrapment in a gel material such as acrylamide taught in U.S. Pat. No. 3,793,445.

Recently, a procedure has been reported which employs polyethylene glycol (PEG) as a precipitating agent in certain RIA techniques such as adsorption, or fractional precipitation of the free and/or bound fraction, and solid phase methods, *Automated Immunoanalysis* (Part 1), edited by Robert F. Ritchie (1978); 67-99; Desbuquois and Aurbach, *J. Clin. Endocrinol. Metab.* 33; 732-738 (1971); Barrett and Cohen, Clin. Chem. 18; 1339-1342 (1972); and Creighton et al., *J. Immunol.* 111; 1219-1227 (1973). In this procedure, polyethylene glycol is added to the test materials after the step of binding by incubation over a period of time. The polyethylene glycol then precipitates antibody-bound component from the unbound component. The disadvantage of this PEG method is that, there is a tendency to increase the non-specific binding of the assay. While this procedure is useful, there has been no suggestion that polyethylene glycol can be employed as a precipitating agent in a double-antibody RIA technique.

In typical double-antibody RIA techniques, the sample of body fluid containing antigen to be assayed is mixed with an antibody specific to the antigen as well as a corresponding radioactive isotope-labeled antigen. The unlabeled and labeled antigen compete for sites on the antibody. A certain time of incubation is allowed for such competitive reaction, and thereafter a second antibody specific to the first antibody, but not to the antigen, is added to agglomerate first antibodies bound to antigen and, generally, after another incubation period of several hours the agglomerate may be separated by centrifugation. The first incubation may proceed until equilibrium is reached before addition of the second antibody, although it is not always essential to reach equilibrium before such addition if the time of incubation is adequate to attain sufficient binding of labeled and unlabeled antigen to produce accurate results, and if a corresponding incubation time is also used for standards of known concentration for preparing a standard curve against which the radioactivity is determined in conventional manner, such as by a gamma-counter or a liquid scintillation-counter.

Among the advantages of the double-antibody technique is that the second antibody is specific to the first but not to the proteinaceous material present in the body fluid and originating from the animal from which the body fluid is taken for assay. Thus, when assaying a human body fluid, for instance, the second antibody does not agglomerate protein therein of human origin that may be present in the human body fluid in which the antigen is to be measured and that may interfere with the assay. Such human body fluid may be blood, blood serum, blood plasma, urine, lymph, bile, spinal fluid, saliva or other glandular secretions or extracts. The technique may also be employed, however, for assaying antigen in fluids from other animals than the human being.

In typical double-antibody procedures heretofore employed, both antibodies are soluble in the aqueous body fluid containing antigen to be assayed. Addition, to the first antibody carrying the labeled and unlabeled antigen, of the second antibody which is not specific to the antigen to be assayed but which is specific to the first antibody, results in a mutual agglomeration of the antigen-carrying first antibodies and second antibodies to give a product of sufficient particle size to be capable of separation by centrifugation. In such procedures, however, relatively large amounts of the second antibody, which is typically quite costly, may be required to achieve a product agglomerate capable of being separated from its supernatant solution containing free antigen. Furthermore, as mentioned briefly above, in the double-antibody procedures heretofore employed a subsequent and sometimes quite lengthy incubation period typically may be required to achieve agglomerates capable of successful separation by centrifugation.

The present invention is thus concerned with providing a double-antibody RIA technique and product wherein the amount of second antibody required to achieve separation of the agglomerates is diminished and is sometimes only about one half of the amount otherwise required. Also, according to the present invention, incubation time of the reaction medium after addition of a second antibody reagent is either diminished or eliminated entirely, while at the same time separation of the macromolecular agglomerates from the supernatant fluid is very satisfactory, thus significantly lessening the time required by the laboratory technician to perform an assay.

Accordingly, the present invention relates to a double antibody, radioimmunoassay method for determining antigens in a sample wherein polyethylene glycol having a molcular weight of from about 2,000 to about 10,000 is provided in a reaction medium in an amount sufficient to accelerate an immunoprecipitation reaction between water-soluble first antibodies in a first antibody reagent bound to antigens and water-soluble second antibodies in a second antibody reagent which are not specific to said antigens to be assayed but which are specific to said first antibodies.

The present invention also relates to a package for a double antibody radioimmunoanalysis of a sample for an antigen. The package may have four or fewer separate components wherein there is provided: a radiolabeled antigen reagent; a first water-soluble antibody reagent specific to said antigen; a second water-soluble antibody reagent which is not specific to the antigen but which is specific to the first antibody; and the polyethylene glycol (PEG) reagent. Each of the reagents may be provided as separate components in the package to provide a four component package, or one or more of the reagents may be combined to provide a package having fewer than four separate components. For instance, all or part of the PEG reagent to be provided in the reaction medium may conveniently be combined with the second, water-soluble antibody reagent to provide, for instance, a reagent containing a minor amount, from about 4% to 12%, preferably about 5% to 10%, by weight PEG depending upon the molecular weight of the antigen to be assayed. A minor portion of the PEG reagent to be supplied to the reaction medium upon performing the assay may be incorporated in the radiolabeled antigen reagent to provide a reagent containing less than about 6% PEG depending upon the molecular weight of the antigen to be assayed, preferably less than about 4%. Such minor amounts of PEG may serve to enhance the first antibody antigen reaction. With regard to the various reagents of the test package, the active ingredients in the reagents; e.g. radiolabeled antigen, first, water-soluble antibody, second, water-soluble antibody and PEG; may be provided in a minor amount sufficient for performing an assay on a sample by prior dilution in a suitable buffer, typically having a pH of about 4 to 10. The test package may also include in addition to the four or fewer components, additional components containing, for instance, pure antigen reagent for preparation of standard and control samples, as well as apparatus for performing the test, such as bottles for storing the reagents, vials for performing tests and in certain instances for storing reagents, e.g.control and standard samples. The entire package, may, as in the case of the prostatic acid phosphatase test, be stored and shipped in the frozen state, below 0° C. and upon receipt by the user it may be stored at refrigerator temperature, e.g. 2° C. to 8° C., until ready for use.

BRIEF DESCRIPTION OF THE DRAWINGS

FIG. 1 is a PAP sample standard curve.

FIG. 2 shows the relationship between positive PAP serum and a PAP standard curve.

FIG. 3 shows the effect of increasing the amounts of PEG.

As mentioned above the polyethylene glycol polymer of the present invention functions to accelerate immunoprecipitation of the double antibody reaction product. Generally such polymers will have a molecular weight of from about 2,000 to 10,000, preferably about 3,000 to 8,000 and will be provided in the reaction medium in a minor amount of, say, from about 1.0% to about 15%, preferably about 3% to about 12%, e.g. about 7% to 10% based on the weight of the reaction medium. At concentrations of polymer in excess of about 15% by weight or even less depending upon the molecular weight of the antigen, there may be a tendency to precipitate immunoglobulins which are unreacted with the second antibody, and there may be more non-specific precipitation of antigen which is not desired, while at concentrations of polymer of less than about 1% the benefit achieved by the addition may only be minimal. The polymer may be conveniently incorporated in the reaction medium by prior admixture with the second, water-soluble antibody reagent used to perform the assay, or it may be added to the reaction medium either prior to or after addition of the second antibody as a separate reagent. If the polymer is provided in the second antibody reagent, as discussed below, it should be present in an amount which will provide the desired amount of polymer in the reaction medium to accelerate immunoprecipitation of the double antibody reaction product.

The sample to be analysed may be a human body fluid such as blood, blood serum, blood plasma, urine, lymph, bile, spinal fluid, saliva or any other body fluid. Pretreatment of the sample to be analysed may be necessary or desirable and with regard to human blood it has been found, for instance that because extremely hyperlipemic human fluid may tend to produce false positive results, the lipemia may be cleared before or during assaying the sample by, for instance, the procedure set forth in U.S. Pat. Application Ser. No. 027,388 filed Apr. 5, 1979 incorporated herein by reference, assigned to the same assignee as the present application, filed concurrently herewith.

Examples of antigens which can be assayed in accordance with the present invention include prostatic acid phosphatase (PAP), creatine phosphokinase (CPK), human chorionic gonadotropin (HCG), throid stimulating hormone (TSH), luteinizing hormone (LH), human growth hormone (HGH), follicle stimulating hormone (FSH), angiotensin, thyroxine, triiodothyronine, digoxin and digitoxin, although many other antigens or similar materials having antigenic activity may be assayed. Thus, as used herein the term antigen is intended to be generic to (1) an antigen per se and (2) a hapten, which is not per se antigenic, but which can be combined with an antigenic carrier such as a protein, to thereby produce a haptenbound antigenic carrier which on introduction into the bloodstream of a vertebrate, produces an antibody that is specific for the hapten. In particular, it has been found that antigens having a relatively low molecular weight, say less than about 120,000, preferably less than about 100,000 can be advantageously assayed in accordance with the invention. The molecular weights referred to herein are determined by conventional methods, such as gel chromotography or SDS (sodium dodecyl sulfate) electrophoresis. Typically such antigens when bound to an antibody may be rather time consuming to separate from the reaction medium using a conventional double antibody precipitation technique, in the absence of polyethylene glycol in the reaction medium in sufficient amounts to accelerate the separation, and the present invention greatly facilitates such separations.

Radiolabeled antigens which can be used for the assay are, for example, 125-I-prostatic acid phosphatase, 125-I-creatine phosphokinase, 125-I-human chorionic gonadotropin, 125-I-thyroid stimulating hormone, 125-I-luteinizing hormone, 125-I-HGH, 125-I-FSH, 125-I-angiotensin, 125-I-thyroxine, 125-I-triiodothyronine, 125-I-digoxin and 125-I-digitoxin, although 125-I-prostatic acid phosphatase and 125-I-creatine phosphokinase are preferred. Many of these radiolabeled antigens are available commercially and those not so available may be conveniently prepared using well-known techniques. Radioisotopes which can be used to prepare radiolabeled antigens suitable for use in this invention are, for example, $131_I$, $^3H$, $^{14}C$, $^{57}Co$, and $^{75}Se$. The antigen preferably is labeled with $125_I$ or other radioisotope to a specific activity of from about one to about 1,000 microcuries per microgram ($\mu$curies/$\mu$g) of antigen. The radiolabeled antigen may be diluted to provide a radiolabeled reagent capable of ideal stoichiometric association with the antibodies in a reaction medium and optimum assay sensitivity. This dilution may be made with suitable aqueous buffers having a pH of from about 4 to 10. Examples of suitable buffers which may be employed for the dilution include Tris, a commercially-available, aqueous solution containing tris (hydroxymethyl) amino methane; Barbital, a commercially-available, aqueous solution of 5,5-diethyl barbituric acid, and other well-known buffers. The extent, if any, of the dilution may depend upon the initial specific activity and the desired disintegrations per minute (dpm) required to realize optimum counting and sensitivity of the assay. As indicated above part of the PEG required in the reaction medium may be supplied by prior incorporation in, for instance, the radiolabeled antigen buffered reagent to enhance the first antibody-antigen reaction.

A first water-soluble antibody specific to the antigen to be assayed may be prepared by inoculating a host animal other than one of the type from which the sample to be assayed has been obtained with antigen to be assayed. For example, when the sample is a human body fluid the host animal may be a rabbit. After inoculation a period of time is allowed to elapse during which the host will develop antibody, whereupon the anti-serum is bled from the animal to provide a first water-soluble antibody. The first water-soluble antibody may be diluted in a buffer material similar to that used for diluting the radiolabeled antigen to a concentration to obtain the maximum performance in the assay, to provide a first, water-soluble antibody reagent.

A second, water-soluble antibody which is not specific to the antigen but which is specific to the first antibody may be prepared by inoculating an animal different from the one in which the first antibody has been obtained, with gamma-globulin of a normal animal of the type from which the first antibody has been obtained. For instance, gamma-globulin of a normal rabbit may be inoculated into a goat. A serum sample is then bled from the goat after it develops antibodies to the rabbit gamma-globulin to provide a second water-soluble antibody specific to the first antibody, but not specific to the antigen to be assayed. The second, water-soluble antibody may also be diluted in a buffer material similar to that used for diluting radiolabeled antigen and first antibody reagents to a concentration to obtain the maximum performance in the assay. Furthermore, although PEG may be provided in the reaction medium by addition thereto as a separate reagent after or even before addition of the second antibody solution, it is preferred that all or a major portion of the polymer be provided in the reaction medium by prior incorporation in the second antibody reagent. Thus, typically from about 1% to 15% by weight, preferably about 3% to 12% by weight, say about 7 to 9% by weight of the polymer may be included in the second antibody reagent to provide a sufficient concentration of polymer in the reaction medium to accelerate an immunoprecipitation reaction between a first water-soluble antibody carrying radiolabeled or unlabeled antigen.

The RIA test procedure may vary, depending upon a number of factors including the selection of the antigen to be assayed and the mode of incorporation into the reaction medium of the water-soluble, nonionic polymer. In general, however, the test reagents may all be equilibrated to room temperature. Then appropriate quantities of control standards, containing predetermined concentrations of the antigen to be assayed, can be added to a series of the tubes and a sample such as patient's blood, or other body fluid containing an unknown amount of antigen, can be added to another series of tubes. Labeled antigen reagent and first antibody reagent can then be added sequentially to all of the tubes which are then vortexed, covered and incubated. The second antibody reagent can next be added to the tubes. At this time polyethylene glycol is provided in the reaction medium in an amount sufficient to accelerate an immunoprecipitation reaction between water-soluble first antibodies in the medium bound to antigens and water-soluble second antibodies which are not specific to said antigen to be assayed but which are specific to said first antibodies. The tubes are then vortexed and centrifuged. The tubes can be decanted and the supernatant liquid discarded. Typically, according to the invention no incubation of the tubes is required after addition of the second antibody reagent, although the tubes may be incubated in certain applications. The tubes can then be counted and a standard curve constructed using the values obtained from the control standards. An average value can be determined for the unknown sample by plotting the value obtained on the standard curve.

The calculations which are performed to determine unknown antigen quantitatively are based on the conventional methodology. The counts in the tube which contain zero antigen are set at 100% (defined as $B_0$). As antigen in the standard is increased, the counts (defined as B) decrease in the precipitate and these counts are divided by the counts in the zero tube to give $B/B_0$ values. The $B/B_0$ values can be plotted against concentration of antigen on linear graph paper. The logit transformation of $B/B_0$ and log of antigen concentration may be used to convert the sigmoid curve to a straight line.

In some instances it may be desirable to provide a nonspecific control standard which does not contain any specific antibody. This control standard may be used to ascertain the radiolabeled antigen non-specifically separated from the reaction medium. In these instances, the true bond tracer may be determined by subtracting the nonspecific counts from all samples.

The following examples will further illustrate the invention although it will be appreciated that the invention is not limited to these specific examples.

EXAMPLE I

Reagents for use in radioimmunoassay of prostatic acid phosphatase antibody are prepared as follows:

1. A prostatic acid phosphatase (PAP) I-125 reagent is prepared containing 75 to 100 nanograms of prostatic acid phosphatase in 0.1 M phosphate buffer containing 0.2% human serum albumin (HSA), 0.2% sodium azide, 0.1% magnesium 8-aniliso-1-naphthalene sulfonate (mag-ANS), and 4% polyethylene glycol by weight having a molecular weight of 6,000–7,500. The solution contains less than 10 microcuries per vial of iodine-125 on the date of calibration.

2. Prostatic acid phosphatase standards are prepared by making appropriate dilutions of pure prostatic acid phosphatase antigen in pooled female human serum preserved with 0.5% sodium azide. The standards contain 0, 1, 2, 5, 10, 20 and 40 nanograms per milliliter.

3. Prostatic acid phosphatase control sera are prepared by adding pure prostatic acid phosphatase antigen to pooled female human serum to concentrations of approximately 1.5, 12.5 and 25 nanograms per milliliter. The serum base used for this purpose is the same as that used for the prostatic acid phosphatase standards, preserved with 0.5% sodium azide.

4. A first antibody reagent is prepared from antisera which has been bled from a rabbit previously inoculated with prostatic acid phosphatase antigen. The antiserum is diluted 1:80,000 with 0.1 M sodium phosphate buffer at a pH of 7.2 containing 0.5%. Tween 20 surface-active agent.

5. A second antibody reagent is prepared containing a 6.5% by weight solution of polyethylene glycol having a molecular weight of 6,000–7,500 in 0.1 M sodium phosphate buffer containing 0.2% sodium azide. To the polyethylene glycol solution is added 7.5 milliliters of goat anti-rabbit antiserum dropwise per liter of solution. The goat anti-rabbit antiserum is bled from a goat which has been previously inoculated with gamma-globulin from a rabbit.

The above reagents are allowed to equilibrate to room temperature (20° C. to 26° C.). Vials containing the PAP standards are mixed by gentle inversion. Then 200 microlites of each of the standard solutions are added to a series of tubes and 200 microliters of patient's sera is added to another series of tubes. Two hundred microliters of rabbit anti-PAP antiserum reagent are added to all tubes and then 200 microliters of PAP-I-125 reagent are added to all tubes, which are then gently vortexed, covered and incubated overnight (14–20 hours) at room temperature.

One milliliter of the second antibody reagent is added to all tubes which are then vortexed and centrifuged at 3,000 rpm's for 20 minutes at room temperature. The supernatant liquid is decanted from the tubes and discarded.

Each tube is then counted for radioactivity for a period sufficient to accumulate a minimum of 10,000 counts and the net counts per minute (cpm) of each concentration of standard and patient's sample are determined and recorded. The net cpm of each standard, patient, or control serum tube is divided by the average net cpm of the zero ng/ml standard tubes and multiplied by 100. The quotient represents the proportion of PAP-I-125 bound to the antibody in the presence of PAP compared to the amount bound in the absence of PAP (percent $B/B_0$).

A standard curve is constructed by plotting the average percent $B/B_0$ of the duplicate values of each standard on the linear axis of semi-logarithmic graph paper as a function of the concentration of the standards in nanograms per milliliter (see FIG. 1). The average percent $B/B_0$ of the duplicate values of each patient's and control serum is determined, and the PAP concentration for the patient's or control serum's percent $B/B_0$ value from the standard curve is also determined. The prostatic acid phosphatase net cpm's and percent $B/B_0$ values are set forth below in Table 1.

TABLE 1

| Prostatic Acid Phosphatase (PAP) Standard (ng/ml) | Average Net CPM | % B/B0 |
| --- | --- | --- |
| 0.0 | 20124 | 100.0 |
| 1.0 | 18684 | 92.80 |

TABLE 1-continued

| Prostatic Acid Phosphatase (PAP) Standard (ng/ml) | Average Net CPM | % B/B0 |
| --- | --- | --- |
| 2.0 | 17506 | 86.95 |
| 5.0 | 14560 | 72.32 |
| 10.0 | 11232 | 55.79 |
| 20.0 | 8378 | 41.61 |
| 40.0 | 5008 | 24.87 |

EXAMPLE II

Preliminary data on 148 normal male subjects age 23 to 98 years gave values of 0 to 2.0 nanograms prostatic acid phosphatase per milliliter of serum. In a group of 50 female subjects age 23 to 68 years no PAP was detected in the sera. Extremely hyperlipemic sera tended to produce false positive results and it is therefore recommended that the lipemia be cleared before or during assaying the samples. No problems were encountered when using hemolyzed sera at levels of 31 milligrams (1+), 63 milligrams (2+), 94 milligrams (3+) and 125 milligrams (4+) hemoglobin concentration in the sera.

The above data shows that the method is very accurate and reproducible at levels of PAP of 0.5 to 40.0 nanograms per milliliter. Intra-runs and inter-runs on multiple assays have shown coefficients of variation of less than 10%. The non-specific binding is less than 2%, and the method has a sensitivity of 100 picograms (using 200μl serum).

EXAMPLE III

A serum sample from a patient with prostatic carcinoma with a PAP level of 45 nanograms per milliliter was serially diluted (5, 10, 25, 50, 75 and 100%) with 0.0 PAP standard and assayed. Results showed an expected response when plotted as percent $B/B_0$ vs. concentration. FIG. 2 shows the relationship between these serial dilutions and a PAP standard curve.

EXAMPLE IV

One milliliter of a second antibody reagent containing 8.4% polyethylene glycol having a molecular weight of 6,000–7,500, a one to 350 dilution of a secondary antiserum, and 0.04%, of Triton X-100 in normal saline solution is added into a preincubated radioimmunoassay reaction medium containing 0.2 milliliter of patient's serum (or standard's), 0.1 milliliter first antibody reagent, and 0.1 milliliter I-125 labeled creatine phosphokinase (CPK-BB) solution. After mixing, the tube is subjected to centrifugation without any incubation, the supernatant (free antigen) is decanted and the precipitate containing antigenantibody complex is measured for radioactivity. The results were as shown in Table 2.

TABLE 2

| CPK-MB Standard IU/l | Average Net CPM | % B/B0 |
| --- | --- | --- |
| 0.0 | 10802 | 100.0% |
| 2.0 | 10017 | 92.7% |
| 10.0 | 7998 | 74.0% |
| 40.0 | 4775 | 44.2% |
| 100.0 | 3004 | 27.8% |

EXAMPLE V

The same procedure outlined with regard to Example IV was followed except that the polyethylene glycol was not included in the reaction medium. It was very difficult to separate a precipitate from the reaction medium using the same amounts of second antibody reagent in the absence of any polyethylene glycol in the reaction medium to accelerate the separation. In several runs additional secondary antiserum was provided and it was determined that approximately twice as much antiserum was required to achieve the same result as was obtained in Example IV and an additional two hour incubation period for separation was also required to achieve acceptable results.

EXAMPLE VI

This example illustrates the use of polyethylene glycol for the separation of an antigen antibody complex from free antigen in a creatine phosphokinase test. The use of a polyethylene glycol at varying concentrations in the reaction medium was evaluated and optimal concentration of polyethylene glycol in the reaction medium was determined.

A creatine phosphokinase-I-125 reagent was prepared as follows:

1. CPK-BB-I-125 is diluted to one part in 500 in a tris buffer solution containing 0.05 M Tris, 0.02 M 2-mercapto ethanol, 0.5mM EDTA, 0.2% BSa, 0.1% sodium azide, 0.01% Triton X-100, pH 8.0. 2. A first antibody reagent is prepared using goat anti-CPK-BB antiserum diluted to one part in 500 with the same tris buffer used in 1. above.

3. A second antibody reagent is prepared by adding anti-goat gamma-globulin antiserum dropwise to a ¼ dilution in the same tris buffer used in 1. above.

4. A separate polyethylene glycol reagent is prepared which includes a polyethylene glycol polymer having a molecular weight of 6,000–7,500 in an amount of about 24% by weight in normal saline solution.

Assays were carried out in a series of tubes by adding for the non-specific binding (NSB) tubes 0.5 ml of $^{125}$I-CPK-BB plus 0.1 ml of a 1:500 dilution of normal goat serum; for the specific binding (SB) tubes, 0.5 ml of $^{125}$I-CPK-BB plus 0.1 ml of a 1:500 dilution of CPK-BB antiserum were added to the tubes. The tubes were incubated at room temperature for a period of 3 hours, after which 0.1 milliliter of the second antibody solution was added to all tubes. To the tubes, enough of the PEG solution was added to the tubes to give the following final concentrations of the PEG in the tubes: 0.1%, 2.0%, 3.0%, 3.5%, 5.0% and 6.0%. The tubes were all vortexed well and incubated an additional one hour at room temperature, whereupon they were centrifuged at 7,500 rpm's for 15 minutes at about 4° C. The supernatant liquid in the tubes was aspirated off and the tubes were counted for one minute. The results, tabulated below in Table 3 and graphed in FIG. 3, indicate that with increasing amounts of polyethylene glycol concentrations, the percent B/T (CPK bound to antibody ÷ total CPK added) of the test increase with no appreciable increase in nonspecific bonding (NSB).

Using no polyethylene glycol, a comparable binding was obtained with a two hour incubation using the same second antibody. Thus, as the above results indicate, the second two hour incubation period is not necessary when the concentration of PEG in the reaction medium is from about 5% to about 6% by weight. Maximum binding using the first antibody and second antibody reagents of this Example has been determined to be about 45% B/T when the first incubation time is about 16 hours at 4° C. and the second incubation time is two hours at room temperature.

TABLE 3

| Conc. of PEG | NSB | Specific Binding (% B/T) |
| --- | --- | --- |
| 0.0% | 1.0% | 32.1 |
| 2.0% | 1.3 | 33.8 |
| 3.0% | 0.9 | 34.6 |
| 3.5% | 1.3 | 34.7 |
| 5.0% | 1.2 | 37.5 |
| 6.0% | 2.1 | 39.8 |

What is claimed is:

1. A double antibody radioimmunoassay method for determining antigens in a sample, comprising providing polyethylene glycol having a molecular weight of from about 200 to about 10,000 in a reaction medium containing labeled antigen, said polyethylene glycol being present in said reaction medium in an amount sufficient to accelerate an immunoprecipitation reaction between water-soluble first antibodies in a first antibody reagent bound to antigens and water-soluble antibodies in a second antibody reagent which are not specific to said antigens to be assayed but which are specific to said first antibodies.

2. The method of claim 1 wherein said polyethylene glycol has a molecular weight of from bout 4,000 to about 7,500.

3. The method of claim 1 wherein said sample is selected from blood serum and blood plasma and said antigen is selected from prostatic acid phosphatase and creatine phosphokinase.

4. The method of claim 1 wherein said first antibody is specific to an antigen selected from prostatic acid phosphatase and creatine phosphokinase.

5. A package for a double antibody radioimmunoanalysis of a sample for an antigen which comprises: a radiolabeled antigen reagent; a first, water-soluble antibody reagent specific to said antigen: a second, water-soluble antibody reagent which is not specific to the antigen but which is specific to the first antibody, said second antibody reagent containing polyethylene glycol having a molecular weight of from about 2,000 to 10,000 in an amount sufficient to accelerate separation of the reaction product of second, water-soluble antibody reagent and antigen bound to said first antibody reagent in a reaction medium.

6. A package for a double antibody radioimmunoanalysis of a sample for an antigen which comprises: a radiolabeled antigen reagent; a first water-soluble antibody reagent specific to said antigen; a second, water-soluble antibody reagent which is not specific to the antigen but which is specific to the first antibody, and a polyethylene glycol reagent containing polyethylene glycol having a molecular weight of from about 2,000 to 10,000 in an amount sufficient to accelerate separation of the reaction product of second, water-soluble antibody reagent and radiolabeled antigen bound to said first antibody reagent in a reaction medium.

7. The package of claim 5 or 6, which also includes pure antigen reagent for preparation of standard and control samples.

8. The package of claim 5 or 6, wherein sad reagents are provided in an aqueous solution having a pH of about 4 to 10.

9. The package of claim 5 or 6, wherein said antigen is selected from prostatic acid phosphatase; and creatine phosphokinase.

* * * * *